Figure 1:
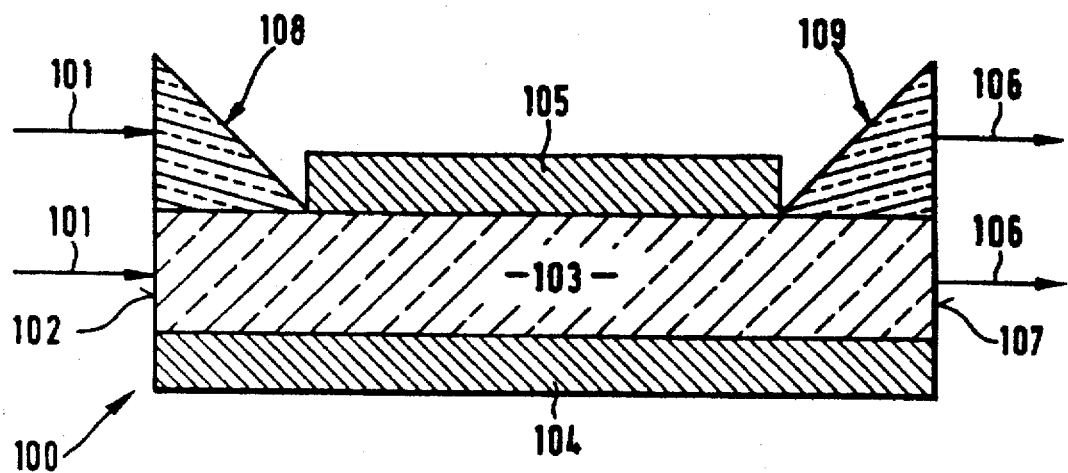

United States Patent [19]

Cabrera et al.

[11] Patent Number: 5,684,165
[45] Date of Patent: *Nov. 4, 1997

[54] SUBSTITUTED THIENO[3,2B]THIOPHENES AND THEIR USE

[75] Inventors: Ivan Cabrera, Dreieichenhain; Uwe Falk, Wiesbaden; Werner Hickel, Ludwigshafen, all of Germany; Donald Lupo, Kawagoe, Japan; Ude Scheunemann, Liederbach/Taunus, Germany; Peter Boldt; Martin Blenkle, both of Braunschweig, Germany

[73] Assignee: Hoechst Aktiengesellschaft, Frankfurt, Germany

[*] Notice: The portion of the term of this patent subsequent to Oct. 7, 2013, has been disclaimed.

[21] Appl. No.: 423,006

[22] Filed: Apr. 14, 1995

Related U.S. Application Data

[62] Division of Ser. No. 133,502, Oct. 7, 1993, Pat. No. 5,432,286.

[30] Foreign Application Priority Data

Oct. 10, 1992 [DE] Germany .................. 42 34 230.9

[51] Int. Cl.⁶ .................. C07D 495/04; G02B 6/02; G02F 1/35
[52] U.S. Cl. .................. 549/50; 385/143; 359/326
[58] Field of Search .................. 549/50; 385/143; 359/326

[56] References Cited

U.S. PATENT DOCUMENTS

| | | | |
|---|---|---|---|
| 4,639,328 | 1/1987 | Krause et al. | 252/299.61 |
| 4,876,271 | 10/1989 | Hartman et al. | 514/443 |
| 5,156,744 | 10/1992 | Rideout et al. | 210/698 |
| 5,432,286 | 7/1995 | Cabrera et al. | 546/270 |

FOREIGN PATENT DOCUMENTS

| | | |
|---|---|---|
| 0144013 | 6/1985 | European Pat. Off. . |
| 0384811 | 8/1990 | European Pat. Off. . |
| 3917323 | 11/1990 | Germany . |

OTHER PUBLICATIONS

Chemical Abstracts, vol. 101, No. 19, 5 Nov. 1984, Abstract No. 170315c, Bertinelli, F. et al. p. 626, col. 2.
Patent Abstracts of Japan, vol. 15, No. 193, 17 May, 1991.
Chemical Abstracts, vol. 115, 1991, p. 844, 15: 83702X.

*Primary Examiner*—José . G. Dees
*Assistant Examiner*—Mary C. Cebulak
*Attorney, Agent, or Firm*—Curtis, Morris & Safford, P.C.

[57] ABSTRACT

Compounds of the formula I

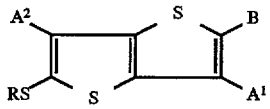

in which

R is a $C_1$- to $C_{22}$-alkyl radical, $A^1$ and $A^2$ are hydrogen or methyl or, $A^1$ is hydrogen and $A^2$ is the nitro group, and B is the cyano group, the nitro group or an electron-attracting organic group having a double bond which is in conjugation with the thieno[3,2-b]thiophene ring system, have a high dipole moment and a high polarizability and are suitable for purposes of nonlinear optics. If R in the formula I is a $C_{12}$- to $C_{22}$-alkyl radical, monomolecular layers can be applied to a substrate by the Langmuir-Blodgett method. The resulting layer elements are suitable, inter alia, as waveguides.

5 Claims, 4 Drawing Sheets

SUBSTITUTED THIENO[3,2B]THIOPHENES AND THEIR USE

This application is a division of application Ser. No. 08/133,502, filed Oct. 7, 1993, now U.S. Pat. No. 5,432,286.

The invention relates to thieno[3,2-b]thiophenes which are substituted by an alkylthio group (electron donor) and an electron acceptor group, and to processes for the preparation of these compounds. The invention also relates to layer elements which contain these compounds in the form of monomolecular layers on a support, and to the use of the compounds for purposes of nonlinear optics.

Because of the different substituents, the molecules of the said compounds are non-centrosymmetrical. They will therefore have in most cases a dipole moment. They also have an extended pi-electron system with several chromophores. This makes them suitable for purposes of nonlinear optics.

Nonlinear optics (NLO) make it possible, inter alia, by means of suitable instruments to obtain from two light beams of different frequency a new frequency which corresponds to the difference or the sum and to obtain from a light beam of one optical frequency optical signals having a multiple of this frequency (in particular twice this frequency). Nonlinear optics also allow electrical information to be converted into optical information and therefore possibly leads in the long term to a fundamental change in the technology of data transmission and data storage.

NLO materials are suitable for the preparation of nonlinear optical components, for example electro-optical modulators, electro-optical switches, electro-optical directional couplers and frequency doublers. These components are used, for example, in optical communications technology (for modulating and controlling optical signals), as spatial light modulators in optical signal processing, for frequency-doubling of semiconductor lasers, for optical data storage, sensor technology and xerography.

A large number of inorganic crystals such as, for example, potassium dihydrogenphosphate and lithium niobate have been investigated as NLO materials. Modulators composed of lithium niobate and frequency doublers based on potassium dihydrogenphosphate are commercially available.

In addition, however, organic NLO materials are of great interest. There are several reasons for this. On the one hand, the NLO activity (=NLO susceptibility) of organic materials is frequently much higher than in the case of inorganic materials. The refractive index and the dielectric constant are in general lower. This allows larger internal electric fields, small polarizations and lower reflection losses, all of which lead to higher efficiency.

Organic materials can also be prepared by a "tailor-made" synthesis, for example with the object of obtaining materials having a high transparency at a defined working wavelength. Organic materials can be processed in many ways. The preparation of monomolecular films of organic materials is simpler than, for example, the preparation of inorganic crystals. These crystals must be grown at relatively high temperatures, then cut, polished and oriented. There is therefore a demand for organic materials for applications in the field of non-linear optics of second order and third order.

The (macroscopic) polarization P induced in a medium by an electric field can be developed in a power series of the electric field strength E.

$$P = X^{(1)}E + X^{(2)}E^2 + X^{(3)}E^3 + \ldots$$

The $X^{(i)}$ are the so-called electric susceptibility functions. The susceptibilities $X^{(2)}$ and $X^{(3)}$ depend on the so-called molecular hyperpolarizabilities $\beta$ and $\gamma$.

$$X^{(2)}(-\omega 3, \omega 2, \omega 1)_{XYZ} = Nf_{x,\omega 3}f_{Y,\omega 2}f_{Z,\omega 1}D_{XYZxyz}\beta_{xyz} \quad P_1 = \sigma E + \beta E^2 + \gamma E^3 + \ldots$$

$P_1$ is here the polarization of the molecule; $\alpha$, $\beta$ and $\gamma$ are polarizabilities. N is the number of molecules per unit volume, f is the local field factor and $D_{XYZxyz}$ is a tensor which describes the orientations of the molecules in the macroscopic system.

As a result of NLO interactions, new frequencies can be generated in an NLO medium, and the refractive index of the medium can be changed.

Important nonlinear optical effects depending on $X^{(2)}$ are the frequency-doubling of a laser beam, the parametric amplification of a weak light signal and the electro-optical conversion of electric signals. To generate second-order effects, the active molecules must be oriented non-centrosymmetrically, since $X^{(2)}$ becomes =0 for centrosymmetrical molecules or crystals.

Attempts can be made to grow crystals of the NLO compounds. If these crystallize non-centrosymmetrically, the crystal has (without further treatment) a nonvanishing macroscopic second-order susceptibility $X^{(2)}$. With crystals, a very high concentration of the chromophore and a very high order are achieved, and also there are no problems with relaxation of the order, since the non-centrosymmetrical order represents the state of lowest free energy. However, the processability of many crystals is poor and the production of integrated optical components with single crystals is in most cases impractical. Moreover, non-centrosymmetrical molecules can also lead to centrosymmetrical crystals.

The process of generating thin layers according to Langmuir-Blodgett (=LB process) probably allows the widest freedom in chemical planning, but it requires extensive experience. In this process, molecules are spread on a water surface, arranged in parallel by reducing the area per molecule and, with constant shear, applied to a substrate by immersing a support and withdrawing it. One monomolecular layer is transferred per immersion step, while maintaining its order. For building up LB layers, amphiphilic molecules are used, i.e. molecules which have a hydrophilic end (a "head") and a hydrophobic end (a "tail").

In order to make possible LB layers with high second-order susceptibilities, organic compounds are prepared which have both high molecular second-order hyperpolarizabilities $\beta$ and amphiphilic properties.

If an amphiphilic material composed of a single molecule species is arranged in multilayers by the LB process, three different possibilities of the immersion behavior can occur: films of the X type (transfer only during the Immersion) or of the Z type (transfer only during withdrawal) can occur, which both have the advantage of the non-centrosymmetrical structure. In most cases, however, films of the Y type are obtained (transfer during immersion and taking-out), in which the molecules show a head-head and tail-tail arrangement.

In most cases, Y-type films show a centrosymmetrical structure. In the few compounds which have an orientation in the support plane (i.e. which have a non-centrosymmetrical structure), the achievable susceptibility is relatively low. In order to obtain a multi-layer arrangement of non-centrosymmetrical structure with compounds which lead to type Y films, three strategies can be applied:

a) A film is formed in which active layers and inactive layers (amphiphilic molecules without chromophore or polymers without chromophore, for example trimethylsilyl-cellulose or polymethacrylates) alternate. This method has the disadvantage that the NLO-active molecules do not efficiently exploit the available volume, since the inactive layers lead to a "dilution" of the system. Such films therefore show a lower NLO activity.

b) The transfer process is controlled in such a way that Z-type films are obtained. This requires, however, special multi-chamber installations for the coating of the substrates. Immersion and removal take place in different chambers.

c) Films of two different NLO-active amphiphilics, whose dipole moments are in one case pointing to the hydrophobic long-chain alkyl radical (tail) and, in the other case, face away from the latter, are alternately transferred. In this case the dipole moments of two adjoining layers will not cancel out, in spite of the Y structure, but will add to one another. The effective dipole moment is therefore still of an order of magnitude which makes it of interest for NLO purposes.

It is always desirable that the NLO-active compound has the largest possible optical nonlinearity $\beta$ (=second-order hyperpolarizability). A compound has a large $\beta$ value, if it contains a conjugated electron system (for example the stilbene radical) and if there is at least one electron donor and at least one electron acceptor group. The value of $\beta$ is enhanced if the molecule absorbs light in the wave region of the incident electric field or of the field generated by NLO (so-called resonance amplification). However, absorptions are undesired for many applications, since they cause losses and adversely affect the optical stability. A compound is regarded as "optically stable" if it can endure the light intensity for a prolonged period without permanent damage to the material. An ideal compound would have a high hyperpolarizability $\beta$, but no residual absorption in the desired wavelength region. However, most compounds having a sufficiently high value for $\beta$ still show considerable residual absorption at the wavelengths desired for frequency-doubling, In particular in the region of 415 nm, which is obtained by frequency doubling of IR light of frequency 830 nm (diode laser).

It was therefore the object to provide organic compounds having a chromophore, whose absorption maximum is below 500 nm, in particular below 450 nm and especially below 400 nm, and which at the same time show good stability (towards the atmosphere, towards elevated temperatures and light) and a high NLO activity.

It is known from J. Med. Chem. 74(6), 1805, and U.S. Pat. No. 4,876,271 that thieno[3,2-b]thiophenes of the formula

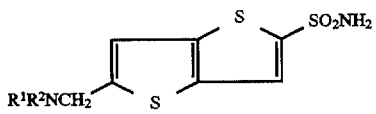

in which
R$^1$ is, for example, methyl or isobutyl and
R$^2$ is, for example, hydrogen,
are suitable for medicamentary treatment of glaucoma. There is no information about the suitability of these compounds for NLO purposes.

Novel thieno[3,2-b]thiophenes of the formula (I)

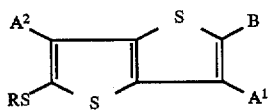

have now been found, in which
R is a C$_1$- to C$_{22}$-alkyl radical,
A$^1$ and A$^2$ are hydrogen or methyl, or
A$^1$ is hydrogen and A$^2$ is the nitro group, and
B is the cyano group, the nitro group or an electron-attracting organic group having a double bond which is in conjugation with the thieno[3,2-b]thiophene ring system.

In particular, B represents the groups

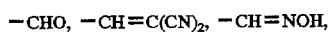

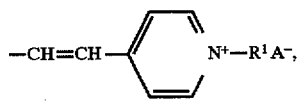

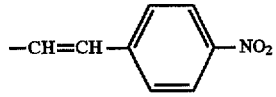

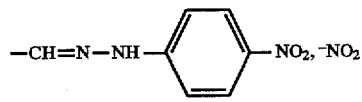

where R$^1$ is a C$_1$- to C$_{22}$-alkyl radical and A is an anion, for example methylsulfate or iodide.

The majority of these compounds has only a very slight absorption or none at all in the visible region.

Compounds of the formula I, in which R is a C$_{12}$–C$_{22}$-alkyl radical, in particular a C$_{16}$–C$_{22}$-alkyl radical, have a long-chain hydrophilic and a relatively hydrophilic electron acceptor group. Such compounds can be arranged by the Langmuir-Blodgett process in the form of monomolecular multilayers on supports.

The invention therefore also relates to a layer element which contains at least one monomolecular layer composed of a compound of the formula I.

To prepare layer elements according to the invention with Langmuir-Blodgett films, the amphiphilic compounds are applied in a highly volatile solvent to a clean water surface (spread). The mean area per molecule can be calculated from the dimension of the surface, the spreading volume and the concentration of the solution. Phase transitions during the compression of the molecules can be monitored by the shear area isotherm.

By means of a barrier or other technique, for example utilization of hydrodynamic forces, the molecules are pushed together, the chains being oriented with increasing density essentially perpendicular to the boundary layer. During the compression, a highly ordered, monomolecular film, whose constant layer thickness is determined by the chain length of the molecules, is formed by self-organization of the molecules in the boundary layer. The typical thickness of such a film is between 2 and 3 nm.

Suitable supports are solids having clean surfaces, such as, for example, glass plates, ceramic plates or metal plates, plastic layers of, for example, PMMA, polystyrene, polycarbonate, polyethylene, polypropylene or polytetrafluoroethylene, or metal layers on the said substrates.

For an experimental determination of the value of the second order susceptibility (X$^{(2)}$) in Langmuir-Blodgett films, the phenomenon of optical frequency-doubling can be used, in which a laser beam of frequency $\omega$ is converted in an active substance into a beam of frequency $2\omega$. In this case, the intensity of the generated harmonic at $2\omega$ increases with the square of the incident intensity of the fundamental beam at $\omega$. More frequently, the method of the so-called "maker-fringes" is used, which is briefly described here.

As the source of the electromagnetic wave at the angular frequency $\omega$, typically an Nd: YAG laser is used which generates a brief (typically 30 ps-30 ns) light pulse at the wavelength 1064 nm ($\omega=9398$ cm$^{-1}$). The light pulse is divided by a beam divider into two beams in a sample channel and a reference channel. In the sample channel, the layer system to be measured is mounted on a rotary table. A small part of the incident beam at 1064 nm is converted by the NLO-active system into a beam at 532 nm, i.e. at the doubled frequency. The intensity of the harmonic wave is measured by a photomultiplier, detected by data acquisition electronics and a control computer as a function of the angle of incidence and averaged over a plurality of shots per angle. Polarization elements and filters ensure that only the harmonic wave generated in the sample is measured under controlled polarization conditions.

An NLOoactive substance, for example pulverulent 2-methyl-4-nitroaniline, is likewise mounted in the reference channel; it serves for compensating the scattering of the measured intensity, caused by fluctuations in the energy and the beam profiles in time and space. In the sample channel, a calibrated sample, for example a quartz crystal whose susceptibility is about 1 pro/V, is then measured. From the angle dependency of the harmonic intensity and the value of the latter as compared with the intensity of the calibrated sample, the NLO susceptibility and the information for orienting the chromophores can be obtained.

The NLO activity of a crystal, in particular a crystal composed of a compound according to the invention, can be investigated by the so-called Kurtz powder method. The compound to be investigated is commuted in a mortar and held fixed in an about 0.2 mm thick layer between two microscope glass slides. A similar procedure is used with the reference sample (for example 2-methyl-4-nitroaniline). The samples are irradiated by a pulsed Nd:YAG laser, and the intensity of the forward-scattered light at 532 nm is measured by a photomultiplier for the sample and for the reference.

In donor-acceptor systems, the molecular hyperpolarizability $\beta$ can be estimated by determining the integrated intensity of the absorption band and the shift of the absorption maximum in different solvents. This method is based on the assumption that the optical non-linearity is dominated by the charge shift between the ground state and the first electronically excited state. In this case, $\beta$ is proportional to the transition moment for the absorption of lowest energy, which can be determined by measuring the integrated band intensity. The hyperpolarizability is also proportional to the difference between the dipole moments of the two states. This difference can be estimated by the shift of the absorption wavelength between two solvents having different dielectric constants.

The compounds according to the invention make it possible to prepare, especially if they are present as a Langmuir-Blodgett film in a layer element or in the form of a non-centrosymmetrical crystal, an optical system having good non-linear optical properties. Such systems are suitable, for example, for electro-optical switches, diode laser frequency-doublers or optical parametric amplifiers (for example as so-called refreshers of weak light signals in optical signal transmission networks).

The figures which follow explain the principle of the construction of a corresponding component.

FIG. 1 represents a component (100) for doubling the frequency of a lightwave. Between a substrate (support) 104 and a cover layer 105, the NLO-active layer 103 is embedded. The refractive index of (103) and (105) should be lower than that of 104, so that total reflection is possible.

The light 101 (for example 830 nm) is coupled in through the end face 102 of the layer 103 or through a prism 108 or a grating (not shown). The cover layer (105) only serves to protect the active layer and can also be omitted. The active layer 103 can also be laterally structured, so that the light is guided in two dimensions (perpendicular to and parallel to the layer plane).

The active layer contains a thieno[3,2-b]thiophene compound according to the invention and preferably has a high (more than $10^{-8}$ esu) optical second order susceptibility. If the thickness and width of the layer 103 and the refractive index of the substrate (104) are in the correct ratio to the wavelength of the incident light, correspondence can be accomplished between the phase velocity of the coupled-in normal wave and that of the second harmonic wave. In that case, a particularly great quantity of light of double the frequency (for example 415 nm) is generated in (103). The light beam (106) leaves the NLO-active layer at the other end face (107) or via a prism (109) or a grating (not shown). The light of the incident wavelength can be removed from (106) by means of filters.

In an alternative version (not shown), the waveguide is constructed in such a way that the coupled-in normal wave is guided in the waveguide, but the harmonic wave is coupled out according to the so-called Cerenkov principle into the substrate and leaves the latter at the end face thereof.

Figure 2:
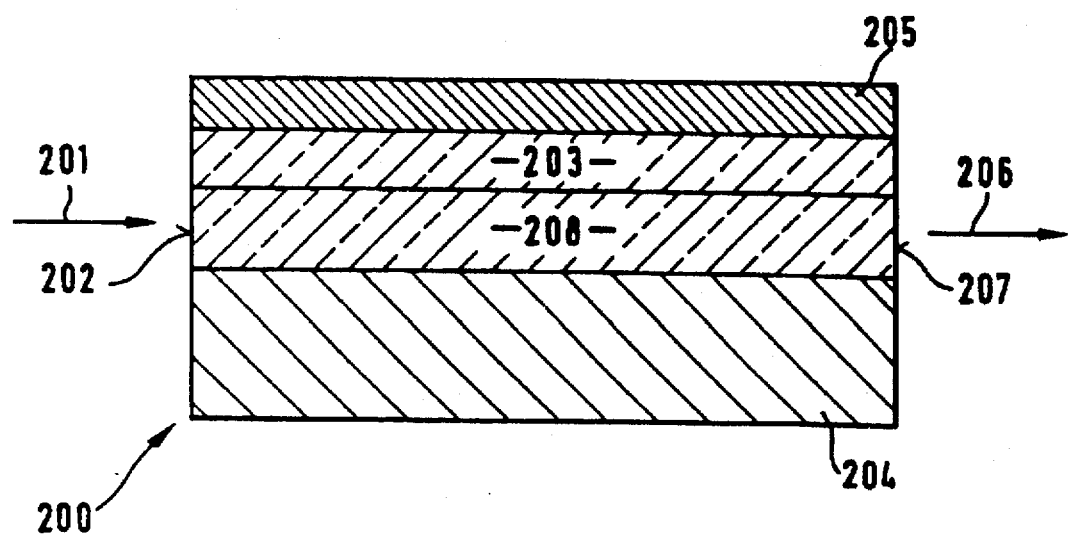

FIG. 2 shows an alternative to this component, with substrate 204 and cover layer 205. The incident light beam 201 enters analogously through the end face 202. The light beam with additional frequency (206) leaves the component through the end face 207. The waveguide is in this case composed of an NLO-inactive layer (203) of high refractive index and an NLO-active layer 208, which contains the compound according to the invention, in particular in the form of an LB multilayer.

Figure 3A:
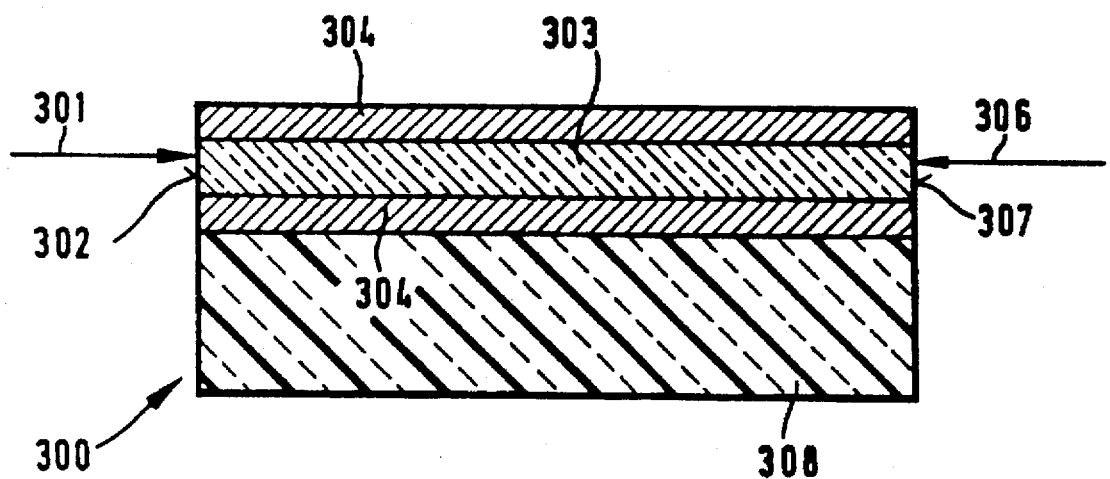
Figure 3B:
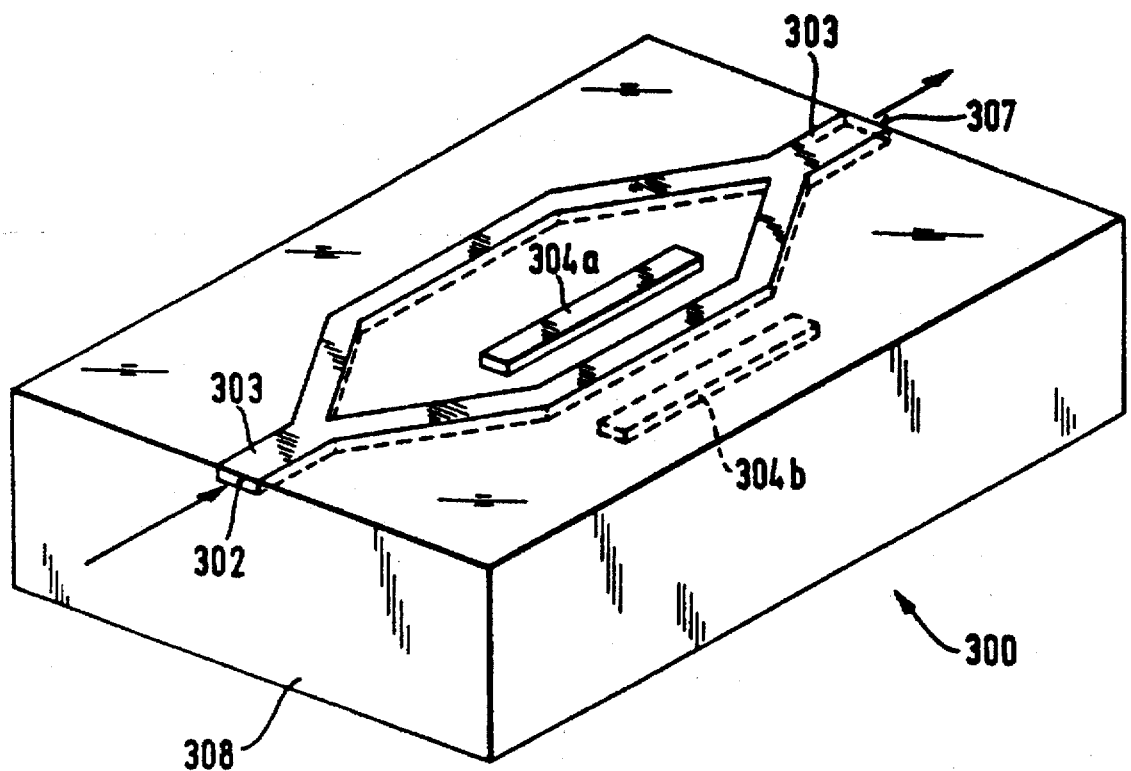

FIGS. 3a and 3b each show a component 300, by means of which the intensity of a lightwave can be modulated. The incident light 301 is launched into the active waveguide layer 303 via the end face 302, a prism (not shown) or a grating (not shown). The layer 303 is laterally structured as a Mach-Zehnder interferometer.

According to FIG. 3a which shows a component in cross section, two electrodes (304) are applied to either side of the waveguide 303 which rests on a transparent substrate. According to FIG. 3b, the electrodes 304 are accommodated with a lateral offset below and above one arm of the interferometer. The interferometer is arranged on a substrate 308.

When a voltage is applied to the electrodes 304, the refractive index In 303 and hence the phase velocity of the light in the particular arm of the interferometer change due to the linear electro-optical effect. This leads to an additive or subtractive superposition of the original wave and altered wave and to a modulation of the intensity of the light which is coupled out via the end face 307.

Figure 4:
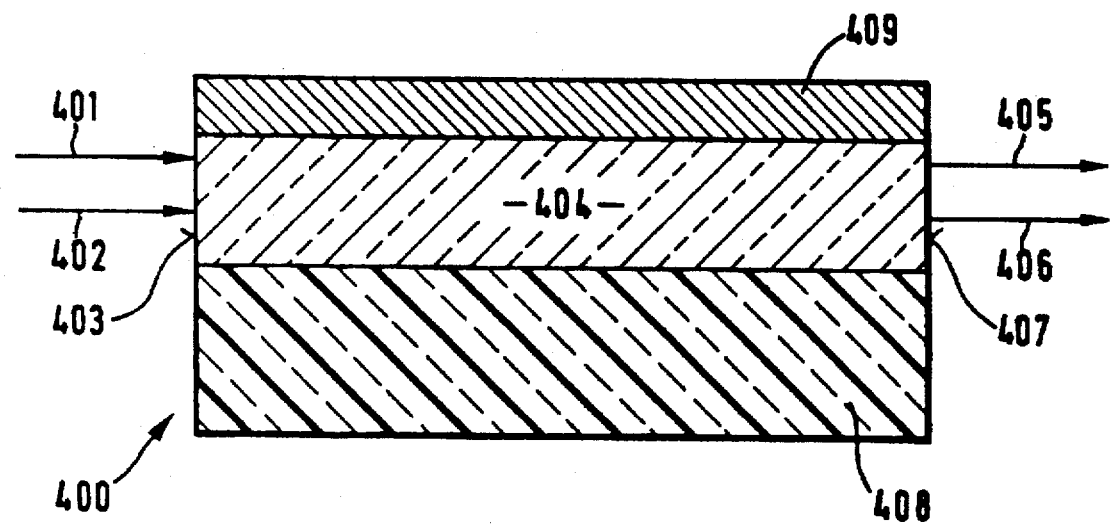

FIG. 4 shows a component 400 in which an Interaction between a first light beam of frequency $\omega 1$ and a second light beam of frequency $\omega 2$ occurs. In this case, new light beams, whose frequencies correspond to the sum ($\omega 3$) and to the difference ($\omega 4$) of $\omega 1$ and $\omega 2$, are generated. The beams of the frequencies ω1 (401) and ω2 (402) are coupled in via the end face 403 or by a prism (not shown) or a grating (not shown) into a waveguide structure 404 which is located on the substrate 408. The waveguide structure 404 can be covered with a protective layer 409.

The active layer 404 having waveguide function can be composed of NLO-active LB multilayers (analogously to FIG. 1 ); it can also have an additional NLO-inactive layer of high refractive index (analogously to FIG. 2).

The layer 404 can also be laterally structured for preparing a two-dimensional waveguide. The frequencies ω1 and ω2 are mixed in the layer 404 by the NLO interaction, i.e. a part of the coupled-in intensity is converted into frequencies which correspond to the sum of the frequencies, and a part corresponds to the difference between the frequencies ω1 and ω2. The light which, inter alia, contains these frequencies can be coupled out via the end face 407 or by a prism (not shown) or a grating (not shown).

The invention is explained in more detail by the examples which follow.

Preparation of novel substituted thieno[3,2-b]thiophenes

Experimental part:

UV/VIS: Hewlett-Packard HP 8425 Diode Array Spectrophotometer.

MS (70 eV), Finnigan MAT 8430. melting point uncorrected.

TLC: Polygram Sil G/UV$_{254}$ (made by Macherey-Nagel): 0.25 mm silica gel.

Column chromatography: silica gel 60 (made by Merck): Particle size 0.063–0.200 mm.

The starting materials were synthesized by known processes: 2-methylthiothieno[3,2-b]thiophene was prepared by the method of A. Bugge, Chem. Scr. 1973 3, 190. Thieno [3,2-b]thiophene was prepared by the method of Y. Goldfarb et al., Bull. Acad. Sci. USSR. Div. Chem. Sci. (English translation 1965, 486).

3,6-Dimethylthieno[3,2-b]thiophene was prepared by the method of G. Martelli, L. Testafferi, M. Tiecco, J. Org. Chem. 1975, 40, 3384.

Novel substituted thieno[3,2-b]thiophenes

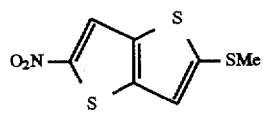

9

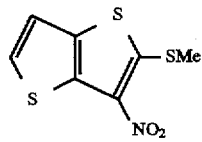

10

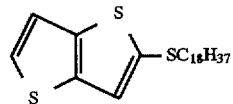

12

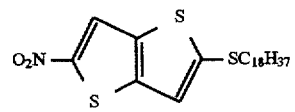

13

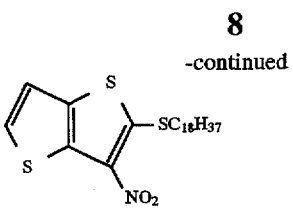

14

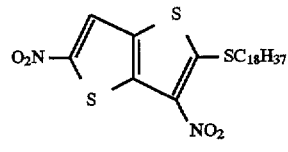

15

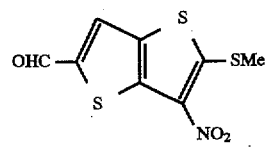

16

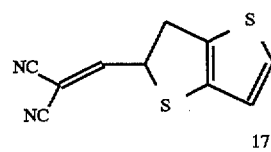

17 R: CH$_3$—
25 R: C$_{18}$H$_{37}$—

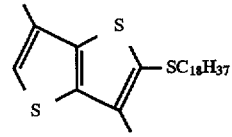

21

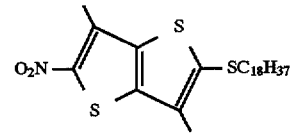

22

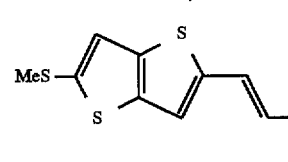

23

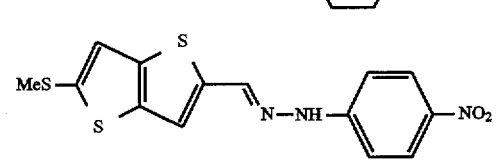

24

1. 2-Methylthio-5-nitrothieno[3,2-b]thiophene (9)

1.0 g (5.4 mmol) of 2-methylthiothieno[3,2-b]thiophene is dissolved in 20 ml of acetic anhydride, and the solution is cooled to −20° C. At this temperature, a mixture of 0.6 ml of 70% nitric acid in 5 ml of acetic anhydride is added dropwise. The mixture is then allowed to warm to room temperature. For working up, the mixture is added to ice water end extracted several times with diethyl ether, and the organic phase is washed with saturated sodium hydrogen carbonate solution until neutral and dried with anhydrous magnesium sulfate. After removal of the solvent in a rotary evaporator under reduced pressure, the orange-yellow crude product obtained is purified by preparative column chromatography (SiO$_2$//2:1 cyclohexane/ethyl acetate, R$_f$: 0.62) and recrystallized from cyclohexane.

Yield: 360 mg (29%) of (9)

Melting point: 119° C.

At the same time, 300 mg (24%) of 3-methylthio-2-nitrotheno[3,2-b]thiophene (10) (R$_f$: 0.42, melting point: 148° C. (cyclohexane)) are obtained as by-product.

UV/VIS (9) $\lambda_{max}$[nm] (lg ε):

| | |
|---|---|
| (acetonitrile) | 408(4.19), 266(3.65), 234(3.75) |
| (chloroform) | 406(4.20), 266(3.68), 242(3.75) |
| (2-propanol) | 398(4.19), 264(3.69), 232(3.79), |
| (n-hexane) | 370(4.20), 262(3.69), 248(3.70), 230(3.72) |

MS (70 eV) m/z(%) (9):
231 (100) [M$^+$], 216 (8) [M$^+$—CH$_3$], 201 (32) [M$^+$—NO], 185 (44) [M$^+$—NO$_2$],
C$_7$H$_5$NO$_2$S$_3$ (231.30) (9):
Calculated: C 36.67 H 2.18 N 6.06 S 41.53
Found: C 36.43 H 2.06 N 5.68 S 41.22
UV/VIS (10) $\lambda_{max}$[nm] (lg ε):

| | |
|---|---|
| (acetonitrile) | 408(3.72), 326(3.66), 284(4.28) |
| (chloroform) | 408(3.96), 326(3.67), 286(4.28), 280 sh (4.23), 242(3.96) |
| (2-propanol) | 400(3.70), 322(3.65), 284(4.26) |
| (n-hexane) | 384(3.73), 320(3.65), 276(4.20), 226(3.88) |

MS (70 eV) m/z(%) (10):
231 (100) [M$^+$], 201 (7) [M$^+$—NO], 184 (26) [201—OH], 152 (29) [184-S]
C$_7$H$_5$NO$_2$S$_3$ (231.30) (10):
Calculated: C 36.67 H 2.18 N 6.06 S 41.53
Found: C 36.37 H 2.17 N 5.74 S 41.40

2. 2-Octadecylthiothieno[3,2-b]thiophene (12)

47 ml (75 mmol) of 1.6N n-butyllithium are added dropwise at room temperature under nitrogen as blanketing gas to 10 g (71 mmol) of thieno[3,2-b]thiophene dissolved in dry diethyl ether. The mixture is then allowed to reflux for 30 minutes. Subsequently, 2.4 g (75 mmol) of dried sulfur are added with ice cooling and vigorous stirring to the resulting suspension of the thieno[3,2-b]thiophenyl lithium salt. The mixture is then allowed to warm to room temperature and stirred for 60 minutes. After renewed cooling by means of an ice bath, 23.7 g (71 mmol) of octadecyl bromide dissolved in 100 ml of dry diethyl ether are then added dropwise. After the mixture has been stirred overnight at room temperature, 50 ml of 25% ammonium chloride solution are added with ice cooling.

For working up, the organic phase is separated off. The aqueous phase is extracted several times with diethyl ether. The combined organic phases are washed with water and dried with magnesium sulfate. After removal of the solvent under reduced pressure in a rotary evaporator, the crude product obtained is purified by preparative column chromatography (SiO$_2$//cyclohexane, R$_f$: 0.41).

The product thus obtained is dried in a high vacuum at 60° C.

Yield: 21.2 g (70%) of 12 Melting point: 46°–47° C.
UV/VIS (12)$\lambda_{max}$[nm] (lg ε):

| | |
|---|---|
| (2-propanol) | 288 sh (4.15), 282(4.21), 274 sh (4.14) |
| (n-hexane) | 288 sh (4.17), 280(4.23), 276(4.17) |

MS (70 eV) m/z(%) (12):
424 (100) [M$^+$], 172 (44) [M$^+$-C$_{18}$H$_{36}$], 171 (38) [M$^+$-C$_{18}$H$_{37}$]
C$_{24}$H$_{40}$S$_3$ (424.76)
Calculated: C 67.86 H 9.49 S 22.64
Found: C 67.80 H 9.50 S 22.60

3. 2-Nitro-5-octadecylthiothieno[3,2-b]thiophene (13)

3-Nitro-2-octadecylthiothieno[3,2-b]thiophene (14) and 3,5-dinitro-3-octadecylthiothieno[3,2-b]thiophene (15)

1.5 g (3.5 mmol) of 2-octadecylthiothieno[3,2-b] thiophene (12) are dissolved in a mixture of 10 ml of acetic anhydride, 10 ml of diethyl ether and 10 ml of cyclohexane. In the course of 15 minutes, this mixture is added dropwise to a solution of 0.36 g (1.5 mmol) of copper nitrate trihydrate [Cu(NO$_3$)$_2$* 3 H$_2$O] in 10 ml of acetic anhydride. Stirring of the mixture is continued for 30 minutes with ice cooling, and the mixture is then allowed to warm and is stirred at room temperature for 3 hours, with monitoring by thin-layer chromatography.

Three nitrated derivatives of 12 are formed.

The mixture is then hydrolysis to 100 ml of ice water and left to stand overnight.

For working up, the crude product/water mixture is extracted with dichloromethane, and the extract is washed with saturated sodium hydrogen carbonate solution and water until neutral and dried with anhydrous magnesium sulfate. After removal of the solvent under reduced pressure in a rotary evaporator, the crude product obtained is purified by preparative column chromatography (SiO$_2$//10:1 cyclohexane/ethyl acetate).

Yield:
320 mg (20%) of (13) R$_f$: 0.78 melting point: 68°–69° C.
380 mg (23%) of (14) R$_f$: 0.59 melting point: 81°–82° C.
330 mg (18%) of (15) R$_f$: 0.16 melting point: 105°–107° C.
MS (70 eV) m/z (%) (13):
469 (100) [M$^+$], 452 (11) [M$^+$—OH], 423 (2) [M$^+$—NO$_2$], 217 (30) [M$^+$—C$_{18}$H$_{36}$], 216 (4) [M$^+$—C$_{18}$H$_{37}$]
MS (70 eV) m/z (%) (14):
469 (100) [M$^+$], 452 (16) [M$^+$—OH], 439 (4) [M$^+$—NO], 217 (14) [M$^+$—C$_{18}$H$_{36}$], 201 (10) [217—O]
C$_{24}$H$_{39}$NO$_2$S$_3$ (469.76) (14)
Calculated: C 61.36 H 8.37 N 2.98 S 20.47
Found: C 61.52 H 8.68 N 2.83 S 20.51
MS (70 eV) m/z (%) (15):
514 (100) [M$^+$], 497 (76) [M$^+$—OH], 262 (10) [M$^+$—C$_{18}$H$_{36}$], 246 (18) [262—O], 229 (7)[246—OH], 197 (7)[229-S]

4. 3,6-Dimethyl-2-octadecylthiothieno[3,2-b]thiophene (21)

3.8 g (22.6 mmol) of 3,6-dimethylthieno[3,2-b]thiophene dissolved in 30 ml of dry diethyl ether are, completely analogously to the preparation of (12), reacted with 17 ml (27.2 mmol) of 1.6N n-butyllithium, 0.9 g (28 mmol) of dry sulfur and 7.7 g (23 mmol) of octadecyl bromide in 30 ml of dry diethyl ether and worked up. The crude product is purified by preparative column chromatography SiO$_2$//n-hexane, R$_f$: 0.58).
Yield: 7.6 g (73%) of (21) Melting point: 48°–50° C.
MS (70 eV) m/z (%) (21):
452 (100) [M$^+$], 200 (58) [M$^+$]—C$_{18}$H$_{36}$, 199 (21) [M$^+$-C$_{18}$H$_{37}$], 167 (9) [199-S]
C$_{26}$H$_{44}$S$_3$ (452.82)
Calculated: C 68.97 H 9.79 S 21.24
Found: C 68.84 H 9.99 S 21.78

5. 3,6-Dimethyl-5-nitro-2-octadecylthiothieno[3,2-b] thiophene (22)

1.5 g (3.5 mmol) of 3,6-dimethyl-2-octadecylthiothieno-[3,2-b]thiophene (21) are dissolved in a mixture of 10 ml of acetic anhydride, 10 ml of diethyl ether and 10 ml of cyclohexane. In the course of 15 minutes, this mixture is added dropwise to a solution of 0.45 g (1.8 mmol) of copper nitrate trihydrate [Cu(NO$_3$)$_2$* 3 H$_2$O] in 15 ml of acetic anhydride, The mixture is then stirred for 4 hours with ice cooling, subsequently added for hydrolysis to 200 ml of ice water and allowed to stand for 4 hours.

For working up, the crude product/water mixture is extracted with diethyl ether, and the extract is washed with saturated sodium hydrogen carbonate solution and water until neutral and dried with anhydrous magnesium sulfate. After removal of the solvent under reduced pressure in a rotary evaporator, the crude product obtained is purified by preparative column chromatography (SiO$_2$//1:1 n-hexane/dichloromethane, R$_f$: 0.56). Final recrystallization from n-hexane gives 22 in the form of yellow needles.
Yield: 1.1 g (67%) of (22)
Melting point: 71°–73° C. (n-hexane)
UV/VIS (22) $\lambda_{max}$ [nm] (lg $\epsilon$):

| (acetonitrile) | 386(4.23), 264 sh (3.67), 246 (3.79) |
| (chloroform) | 392(4.24), 272 sh (3.67), |
| | 260 sh (3.78), 246(3.87) |

MS (70 eV) m/z (%) (22):
497 (100) [M$^+$], 480 (8) [M$^+$—OH], 467 (7) [M$^+$-NO], 451 (5) [M$^+$—NO$_2$], 245 (39) [M$^+$—C$_{18}$H$_{36}$], 244 (9) [M$^+$—C$_{18}$H$_{37}$]
C$_{26}$H$_{43}$NO$_2$S$_3$ (497.81)
Calculated: C 62.73 H 8.71 N 2.81 S 19.32
Found: C 62.88 H 8.87 N 2.79 S 19.36

6. 5-Methylthiothieno[3,2-b]thiophene-2-carbaldehyde (16)

9.5 g (51 mmol) of 2-methylthiothieno[3,2-b]thiophene[1] are dissolved in 12 ml (0.15 mol) of N,N-dimethylformamide. 4.8 ml (51 mmol) of phosphorus oxychloride are then added dropwise in the course of 30 minutes with cooling by means of an ice bath. After stirring for a further 30 minutes, the mixture is allowed to warm to room temperature, An exothermic reaction then starts. After stirring for 45 minutes at room temperature, the mixture is heated for 30 minutes at 80° C. to complete the reaction. After cooling, the mixture is added for hydro-lysis to 150–200 ml of ice water, adjusted by means of ammonium acetate to pH 5–6 and left to stand overnight.

For working up, the crude product is taken up in diethyl ether, washed with saturated sodium hydrogen carbonate solution and with water until neutral and dried with anhydrous magnesium sulfate. After removal of the solvent under reduced pressure in a rotary evaporator, the crude product obtained is purified by preparative column chromatography (SiO$_2$//dichloromethane, R$_f$: 0.60).
Yield: 8.6 g (79%) of (16) Melting point: 73° C.
UV/VIS (16) $\lambda_{max}$ [nm] (lg $\epsilon$):

| (acetonitrile) | 350(4.31), 324 sh (4.19), 260(3.49) |
| (chloroform) | 354(4.29), 330 sh (4.19), 264(3.55) |
| (2-propanol) | 350(4.29), 324 sh (4.20), 262(3.52) |
| (n-hexane) | 334(4.33), 318 sh (4.28), 268 sh (3.55) |

MS (70 eV) m/z (%) (16):
214 (100) [M$^+$], 213 (10) [M$^+$-H], 199 (63) [M$^+$—CH$_3$], dissolved in 15 ml of dry ethanol is then added, and 0.5 ml of piperidine is subsequently added dropwise. After refluxing for 15 minutes, the mixture is allowed to cool slowly to room temperature. The crude product which has precipitated is washed with ethanol and purified by sublimation in a high vacuum (170° C./0.2 mbar).

Yield: 1.1 g (89%) of (17) R$_f$: (CH$_2$Cl$_2$): 0.65
Melting point: 197° C.
UV/VIS (17) $\lambda_{max}$ [nm] (lg $\epsilon$):

| (acetonitrile) | 428(4.56), 286(3.56), 240 sh (3.70) |
| (chloroform) | 438(4.55), 292(3.57), 242(3.79), |
| | 230(3.84) |
| (2-propanol) | 426(4.46), 288(3.68), 230 sh (3.78) |
| (n-hexane) | 428 sh (4.49), 408(4.56), 290(3.61) |

MS (70 eV) m/z (%) (17):
262 (70) [M$^+$], 247 (100) [M$^+$—CH$_3$]
C$_{11}$H$_6$N$_2$S$_3$ (262.36)
Calculated: C 50.36 H 2.31 N 10.68 S 36.66
Melting point: 191° C. (ethanol)
UV/VIS (18) $\lambda_{Amax}$ [nm] (lg $\epsilon$):

| (2-propanol) | 328(4.46), 316(4.26) |
| (n-hexane) | 326(4.42), 312(4.38) |

MS (70 eV) m/z (%) (18):
229 (100) [M$^+$], 214 (68) [M$^+$—CH$_3$], 196 (15) [214—H$_2$O],
186 (17) [M$^+$—CHNO], 170 (19) [214—CH—N—OH]
C$_8$H$_7$NOS$_3$ (229.33)
Calculated: C 41.90 H 3.08 N 6.11 S 41.94
Found: C 41.74 H 2.97 N 6.00 S 41.95

9. 5-Methylthiothieno[3,2-b]thiophene-2-carbonitrile (19)

0.85 g (3.7 mmol) of the oxime 18 are stirred with 3 ml of acetic anhydride and, after 10 minutes, heated at 140° C. for 1 hour. After cooling, 4 ml of water are added end the mixture is refluxed for 10 minutes. The mixture is then allowed to cool down with ice cooling and is rendered alkaline by addition of 10 ml of 2N sodium hydroxidic solution.

For working up, the mixture is extracted with diethyl ether, and the extract is washed with water until neutral and dried with anhydrous magnesium sulfate. After removal of the solvent under reduced pressure in a rotary evaporator, the crude product obtained is purified by preparative column chromatography (SiO$_2$//dichloromethane, R$_f$ 0.74). By final sublimation from the melt (120° C./0.2 mbar), 19 is obtained as pale yellowish crystals.
Yield: 660 mg (84%) of (19) Melting point: 73° C.
UV/VIS (19) $\lambda_{max}$[mn](lg $\epsilon$):

| (acetonitrile) | 324(4.27), 300(4.19) |
| (chloroform) | 322(4.27), 302(4.21) |
| (2-propanol) | 320(4.26), 300(4.21) |
| (n-hexane) | 330 sh (4.16), 312(4.29), 298(4.26) |

MS (70 eV) m/z (%) (19):
211 (64) [M$^+$], 196 (100) [M$^+$—CH$_3$]
C$_8$H$_5$NS$_3$ (211.31)
Calculated: C 45.47 H 2.38 N 6.63 S 45.52
Found: C 45.63 H 2.31 N 6.56 S 45.70

10. 1-Methyl-4-[(5'-methylthio-thieno[3,2-b]thiophen-2-yl)-transethenyl]pyridinium iodide (23)

0.8 g (3.8 mmol) of the aldehyde 16, 1.1 g (4.6 mmol) of 1,4-dimethylpyridinium iodide and 0.5 ml of piperidine are refluxed in 10 ml of dry ethanol for 2.5 hours. After the mixture has cooled to room temperature, the crude product which has precipitated is isolated and recrystallized twice from methanol.

304 (100) [M$^+$-1]

C$_{15}$H$_{14}$NS$_3$I (431.37)

Calculated: C 41.77 H 3.27 N 3.25 S 22.30

Found: C 41.41 H 3.32 N 3.14 S 22.26

11. 5-Methylthiothieno[3,2-b]thiophene-2-carbaldehyde 4'-nitrophenylhydrazone (24)

0.6 g (3.9 mmol) of 3-nitrophenylhydrazine is dissolved in 4 ml of 50% acetic acid, 6 ml of water are added with stirring, and the mixture is heated to 60°–70° C. 20 ml of ethanol are then added to the hot solution. A solution of 0.8 g (3.7 mmol) of the aldehyde 16 in 10 ml of ethanol is then added dropwise to the hot hydrazine solution in acetic acid. After 10 minutes, the mixture is allowed to cool to room temperature and is stirred for 1 further hour. The crude product which has precipitated is then isolated, washed with ice-cold ethanol and recrystallized twice from ethyl acetate. Yield: 890 mg (69%) of (24)

Melting point: 217° C. (ethyl acetate) R$_f$ (CH$_2$Cl$_2$): 0.54

Calculated: C 48.12 H 3.17 N 12.02 S 27.52

Found: C 48.30 H 3.17 N 11.87 S 27.15

12. 2-Dicyanovinyl-5-octadecylthiothieno[3,2-b]thiophene (25)

1.5 g (3.3 mmol) of aldehyde 20 are dissolved in 15 ml of dry ethanol and heated to boiling point. 250 mg (3.8 mmol) of malononitrile dissolved in 10 ml of dry ethanol are then added immediately, and subsequently 0.5 ml of piperidine is added dropwise. After refluxing for 45 minutes, the mixture is allowed to cool slowly to room temperature.

The crude product which has precipitated is isolated and purified by preparative column chromatography (SiO$_2$//2:1 cyclohexane/dichloromethane, R$_f$ 0.64).

Yield: 1.45 g (88%) of (25) Melting point: 102° C.

UV/VIS (25) λ$_{max}$ [nm] (lg ε):

| (acetonitrile) | 416(4.53), 306(3.49) |
| (chloroform) | 426(4.54), 310(3.57) |
| (2-propanol) | 412(4.46), 300(3.71) |
| (n-hexane) | 428 sh (4.44), 408(4.57), 348 sh (3.93), 308 sh (3.61) |

For working up, the mixture is added to 150–200 ml of ice water and stirred for 36 hours, until the light yellow color has changed to light brown. The crude product is then taken up in diethyl ether, washed with saturated sodium hydrogen carbonate solution and with water until neutral, dried with anhydrous magnesium sulfate and freed of the solvent under reduced pressure in a rotary evaporator.

The crude product is purified by preparative column chromatography (SiO$_2$//5:1 dichloromethane/cyclohexane, R$_f$ 0.66).

Yield: 6.7 g (70%) of (20) Melting point: 62° C.

UV/VIS (20) λ$_{max}$ [nm] (lg ε):

| (acetonitrile) | 340(4.31), 324 sh (4.26), 262(3.54) |
| (chloroform) | 344(4.30), 330 sh(4.25), 264(3.55) |
| (2-propanol) | 338(4.31), 322(sh (4.25), 264(3.55) |
| (n-hexane) | 360 sh (4.06), 334(4.35), 320(4.32), 304 sh (4.11), 270 sh (3.55) |

MS (70 eV) m/z (%) (20):

452 (100) [M$^+$], 424 (11) [M$^+$—CO], 200 (68)[M$^+$—C$_{18}$H$_{36}$], 199 (16) [M$^+$—C$_{18}$H$_{37}$], 172 (9) [200—CO], 171 (10) [200—CHO]

14. 5-Methylthio-2-(4'-nitrophenyl-trans-ethenyl)thieno[3,2-b]thiophene

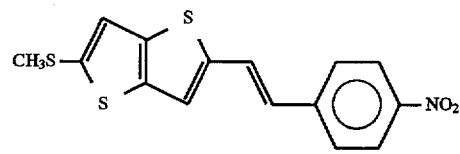

0.80 g (3.7 mmol) of the aldehyde 16, 0.69 g (3.8; mmol) of 4-nitrophenylacetic acid and 0.2 ml of piperidine are heated for 45 minutes at 150°–160° C. The mixture is then allowed to cool to room temperature, the resulting mass is taken up in glacial acetic acid and the mixture is poured into 80 ml of water. The crude product which has precipitated is filtered off with suction, washed with cold ethanol and then purified by sublimation in a high vacuum (190° C./0.07 mbar).

Yield: 750 mg (61%) (27) Melting point: 230° C.

UV/VIS (27) λ$_{max}$ [nm] (lg ε):

| (acetonitrile) | 404(4.55), 318(4.07) |
| (chloroform) | 414(4.54), 318(4.10) |
| (2-propanol) | 404(4.50), 316(4.04) |

(n-hexane) 414 sh (4.33), 394(4.43), 380 sh (4.38, 312(4.16), 258(3.98)

MS (70 eV)m/z (%)(27): 333(100)[M$^+$], 318 (64)[M$^+$—CH], 303(9)[M$^+$—NO], 287(11)[M$^+$—NO$_2$], 272(22)[287-CH$_3$], 240(13)[272-S], 196(9)[318-C$_6$H$_4$NO$_2$]

Elemental analysis (27)

C$_{15}$H$_{11}$NO$_2$S$_3$

Calculated: C 54.03 H 3.33 N 4.20 S 28.84

Found: C 53.99 H 3.09 N 4.28 S 28.82

Further new substituted thieno[3,2-b]thiophenes

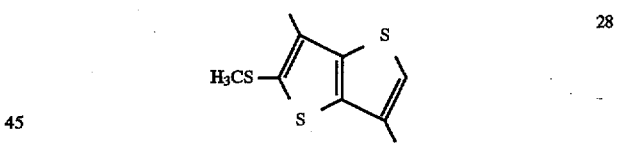

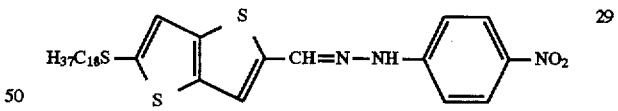

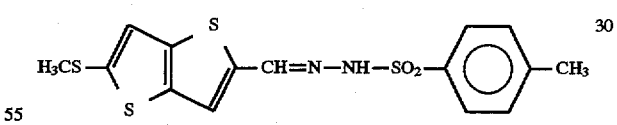

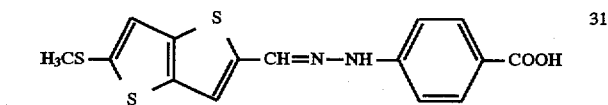

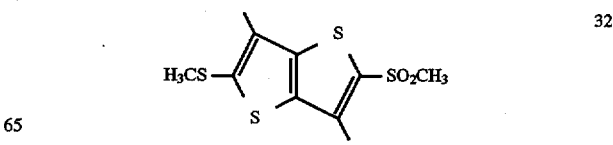

15. 3,6-Dimethyl-2-methylthio-thieno[3,2-b]thiophene (28)

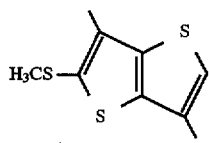

12.0 g (71 mmol) of 3,6-dimethylthieno[3,2-b]thiophene dissolved in 230 ml of dry diethyl ether are reacted with 50 ml (80 mmol) of n-butyllithium (1.6N solution in hexane), 2.40 g (75 mmol) of dry sulfur and 4.7 ml (75 mmol) of methyl iodide analogously to the preparation of 12, and worked up. The crude product is purified by distillation in a high vacuum (boiling point: 104° C./0.2 mbar).

Yield: 13.1 g (91%) 28 Melting point: 49° C.

IR: 3086 cm$^{-1}$, 2915, 2843 (CH)

MS (70 eV) m/z (%) (28):

216, 215, 214 (11, 9, 77) [M$^+$], 201, 200, 199 (15, 12, 100)

$C_9H_{10}S_3$ (214.36)

Calculated: C 50.43 H 4.70 S 44.87

Found: C 50.52 H 4.72 S 44.46

16. 5-Octadecylthio-thieno[3,2-b]thiophene-2-carbaldehyde 4'-nitrophenylhydrazone (29) stirred for a further 2 hours. The crude product which has precipitated is isolated, washed with water and purified by preparative column chromatography (SiO$_2$//5:1 dichloromethane/cyclohexane, R$_f$ 0.45).

Yield: 1.20 g (62%) 29 Melting point: 110°–112° C.

IR: 2919 cm$^{-1}$, 2850 (CH)

MS (70 eV) m/z (%) (29):

590, 589, 588, 587 (6, 21, 38, 100) [M$^+$]

$C_{31}H_{45}N_3O_2S_3$ (587.90)

Calculated: C 63.33 H 7.72 N 7.15 S 16.36

Found: C 63.58 H 7.74 N 6.95 S 16.38

17. 5-Methylthio-thieno[3,2-b]thiophene-2-carbaldehyde tosylhydrazone (30)

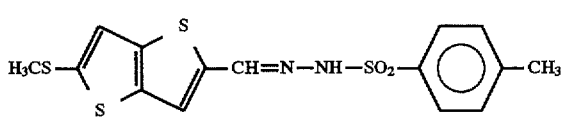

0.75 g (4.0 mmol) of p-toluenesulfonylhydrazine is dissolved in 8 ml of methanol, heated to 60° C. and treated with 0.3 ml of 2N hydrochloric acid. Subsequently, 0.80 g (3.7 mmol) of the aldehyde 16 is added in portions. The mixture is then stirred for 10 minutes and then allowed to cool to room Calculated: C 47.10 H 3.69 N 7.32 S 33.52

Found: C 46.95 H 3.70 N 7.31 S 33.53

18. 4-(N'-(5-Methylthio-thieno[3,2-b]thiophen-2-yl)-methylene-hydrazino)benzoic acid (31):

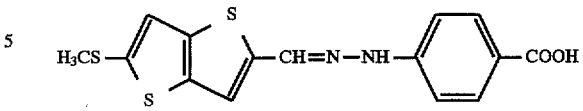

1.0 g (4.7 mmol) of the aldehyde 16 and 0.80 g (5.2 mmol) of 4-hydrazinobenzoic acid are reacted analogously to the preparation of 29. The crude product is purified by recrystallization from ethanol/acetone.

Yield: 0.87 g (53%) 31 Decomposition point: 220° C.

IR: 1667 (C=O) cm$^{-1}$, 1603

UV/VIS (31) $\lambda_{max}$ [nm] (lg ε):

| (Acetonitrile) | 386(4.645), 300(4.231) |
| (Chloroform)   | 388(4.586), 304(4.208) |

MS (70 eV) m/z (%) (31):

350, 349, 348 (3, 2, 11) [M$^+$], 333 (3), 179, 178 (18, 100)

$C_{15}H_{12}N_2O_2S_3$(348.45)

Calculated: C51.70 H 3.47 N 8.04 S 27.60

Found: C51.45 H 3.46 N 8.05 S 27.60

19. 3,6-Dimethyl-2-methylsulfonyl-5-methythiothieno-[3,2-b]thiophene (32)

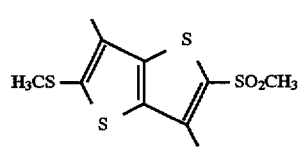

3.3 ml (5.3 mmol) of n-butyllithium (1.6N solution in hexane) are added dropwise at room temperature, under nitrogen as blanketing gas, to 1.0 g (4.7 mmol) of 3,6-dimethyl-2-methylthio-thieno[3,2-b]thiophene (28) dissolved in 20 ml of dry diethyl ether. The mixture is then allowed to reflux for 60 minutes. The resulting solution of the lithium compound is then transferred under blanketing gas and with exclusion of moisture into a dropping funnel and added dropwise to a solution, cooled to –70° C., of 0.80 g (8 mmol) of methanesulfonic acid fluoride in 10 ml of dry ether. The mixture is then allowed to warm to room temperature and stirred overnight.

20 ml of saturated ammonium chloride solution are added to the mixture. The organic phase is separated off and the aqueous phase is extracted several times with dichloromethane. The combined organic phases are washed with water and dried with magnesium sulfate. After the solvent has been removed under reduced pressure in a rotary evaporator, the product 32 is obtained by preparative column chromatography (SiO$_2$//dichloromethane, R$_f$ 0.44). Further purification is carried out by repeated recrystallization from methanol.

Yield: 0.22 g (16%) 32 Melting point: 166° C. (methanol)

IR: 2921 cm$^{-1}$, 2854 (CH), 1305, 1147 (SO)

UV/VIS (32) $\lambda_{max}$ [nm] (lg ε):

| (Acetonitrile) | 314 sh (4.199), 302(4.232) |

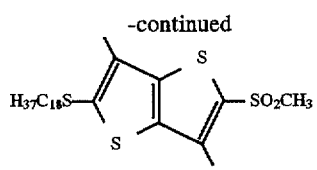

20. 3,6-Dimethyl-2-methylsulfonyl-5-octadecylthio-thieno[3,2-b]thiophene (33)

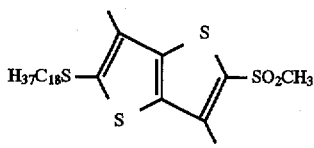

2.0 g (4.4 mmol) of 3,6-dimethyl-2-octadecylthio-thieno[3,2-b]thiophene (21) in 50 ml of dry ether are metalated with 3.5 ml (5.6 mmol) of n-butyllithium (1.6N solution in hexane) as described for the preparation of 32, and reacted at −70° C. with 0.80 g (8.2 mmol) of methanesulfonic acid fluoride. The mixture is then allowed to warm to room temperature and stirred overnight.

20 ml of saturated ammonium chloride solution are added to the mixture. The organic phase is separated off and the aqueous phase is extracted several times with dichloromethane. The combined organic phases are washed with water and dried with magnesium sulfate. After the solvent has been removed under reduced pressure in a rotary evaporator, the product 33 is obtained by preparative column chromatography (SiO$_2$//dichloromethane, R$_f$: 0.44). Further purification is carried out by repeated recrystallization from acetone.

Yield: 0.22 g (10%) 33 Melting point: 105°–107° C. (acetone)
IR: 2921 cm$^{-1}$, 2849 (CH), 1304, 1149 (SO)
UV/VIS (33) $\lambda_{max}$ [nm] (lg ε):

| (Acetonitrile) | 310 sh (4.067), 302(4.102) |
|---|---|
| (Chloroform) | 318 sh (4.233), 306(4.281) |

MS (70 eV) m/z (%) (33):
533, 532, 531, 530 (6, 23, 33, 100) [M$^+$], 280, 279, 278 (15, 8, 80)
C$_{27}$H$_{46}$O$_2$S$_4$ (530.90)
Calculated: C 61.08 H 8.73 S 24.16
Found: C 60.81 H 9.03 S 24.02

21. Methyl 3,6-dimethyl-5-methylthio-thieno[3,2-b]thiophene-2-carboxylate (34)

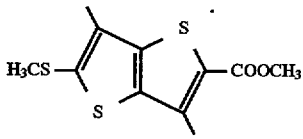

3.0 ml (4.8 mmol) of n-butyllithium (1.6N solution in hexane) are added dropwise at room temperature, under nitrogen as blanketing gas, to 1.0 g (4.7 mmol) of 3,6-dimethyl-2-methylthio-thieno[3,2-b]thiophene (28) dissolved in 20 ml of dry diethyl ether. The mixture is then allowed to reflux for 60 minutes. The resulting solution of the lithium compound is then transferred under blanketing gas and with exclusion of moisture Into a dropping funnel and added dropwise to a solution, cooled to −70° C., of 0.50 g (5.3 mmol) of methyl chloroformate in 10 ml of dry ethyl ether. The mixture is then allowed to warm to room temperature in the course of 2 hours.

20 ml of saturated ammonium chloride solution are added to the mixture. The organic phase is separated off and the aqueous phase is extracted with diethyl ether. The combined organic phases are washed with water and dried with magnesium sulfate. After the solvent has been removed under reduced pressure in a rotary evaporator, the product 34 is obtained by preparative column chromatography (SiO$_2$//dichloromethane, R$_f$: 0.65). Further purification is carried out by recrystallization from ethanol.

Yield: 0.90 g (72%) (34) Melting point: 120° C. (ethanol)
IR: 2940 cm$^{-1}$ (CH), 1699, 1259 (CO)
UV/VIS (34) $\lambda_{max}$ [nm] (lg ε):

| (Acetonitrile) | 322 sh (4.306), 312(4.332) |
|---|---|
| (Chloroform) | 328 sh (4.316), 316(4.347) |

MS (70 eV) m/z (%) (34):
335, 334, 333 (10, 14, 64) [M$^+$], 304, 303, 302 (15, 19, 100), 289, 288, 287 (6, 9, 40)
C$_{11}$H$_{12}$O$_2$S$_3$ (272.40)
Calculated: C 48.50 H 4.44 S 35.31
Found: C 48.55 H 4.14 S 35.30

22. Methyl 3,6-dimethyl-5-octadecylthio-thieno[3,2-b]thiophene-2-carboxylate (35)

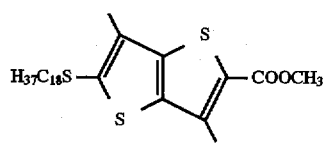

Analogously to the preparation of 34, 3.0 g (6.6 mmol) of 3,6-dimethyl-2-octadecylthio-thieno[3,2-b]thiophene (21) in 50 ml of dry ether are metalated with 4.5 ml (5.6 mmol) of n-butyllithium (1.6N solution in hexane) and reacted at −50° C. with 0.6 ml (7.7 mmol) of methyl chloroformate. After stirring overnight and addition of 20 ml of saturated ammonium chloride solution, the organic phase is separated off and the aqueous phase is extracted with dichloromethane. The combined organic phases are washed with water, dried and freed of solvent. The purification of the crude product is carried out by preparative column chromatography (SiO$_2$//dichloromethane, R$_f$: 0.76) and recrystallization from pentane.

Yield: 1.70 g (51%) 35 Melting point: 71° C. (pentane)
IR: 2917 cm$^{-1}$, 2851 (CH), 1703, 1268 (CO)
UV/VIS (35) $\lambda_{max}$ [nm] (lg ε):

| (Acetonitrile) | 322 sh (4.328), 314(4.362) |
|---|---|
| (Chloroform) | 328 sh (4.328), 318(4.368) |

MS (70 eV) m/z (%) (35): 513, 512, 511, 510 (6, 19, 34, 100) [M$^+$], 258 (76) [M$^+$—C$_{18}$H$_{36}$]
C$_{28}$H$_{46}$O$_2$S$_3$ (510.85)
Calculated: C 65.83 H 9.08 S 18.83
Found: C 65.61 H 9.15 S 18.87

23. 3,6-Dimethyl-5-methylthio-thieno[3,2-b]thiophene-2-sulfonic acid amide (36)

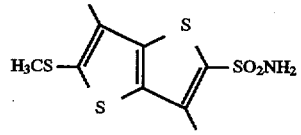

5.0 ml (8.0 mmol) of n-butyllithium (1.6N solution in hexane) are added dropwise at room temperature under nitrogen as blanketing gas to 1.5 g (7.0 mmol) of 3,6-dimethyl-2-methylthiothieno[3,2-b]thiophene (28) dissolved in 25 ml of dry diethyl ether. The mixture is then allowed to reflux for 60 minutes. After cooling the mixture to −40° C., dry sulfur dioxide is introduced for 60 minutes with vigorous stirring. The mixture is then allowed to warm to room temperature, the sulfur dioxide is allowed to evaporate and the solvent is distilled off at room temperature. The resulting crude lithium sulfinate is taken up in 40 ml of saturated sodium hydrogen carbonate solution and, with ice cooling, treated with 1.5 g (11.2 mmol) of N-chlorosuccinimide and stirred for 60 minutes at 0° C. The mixture is then extracted with chloroform and the extract is dried. After removal of the solvent in a rotary evaporator, the crude sulfonyl chloride is dissolved in acetone, treated dropwise with 20 ml of concentrated ammonia solution with ice cooling, and left to stand overnight. For working up, the ammonia and acetone are removed in a rotary evaporator, and the crude product which has thus precipitated is filtered off and washed with dichloromethane. Further purification is carried out by sublimation in a high vacuum (190° C./0.5 mbar) and subsequent recrystallization from ethanol.

Yield: 0.95 g (46%) 36 Melting point: 217° C. (ethanol)
IR: 3305 cm$^{-1}$, 3234 (NH), 1326, 1155 (SO)
UV/VIS (36) $\lambda_{max}$ [nm] (lg ε):

| (Acetonitrile) | 308 sh (4.240), 300(4.280) |
| (Chloroform) | 312 sh (4.237), 304(4.272) |

MS (70 eV) m/z (%) (36):
295, 294, 293, (19, 14, 100) [M$^+$], 280, 279, 278 (15, 8, 80)
C$_9$H$_{10}$NO$_2$S$_4$ (293.43)
Calculated: C 36.84 H 3.78 N 4.77 S 43.70
Found: C 36.93 H 3.67 N 4.64 S 43.76

24. 3,6-Dimethyl-5-methylthio-thieno[3,2-b]thiophene-2-carbaldehyde (37)

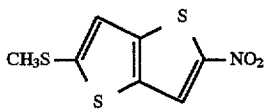

1.50 g (7.0 mmol) of 3,6-dimethyl-2-methylthio-thieno[3,2-b]thiophene (28) are dissolved in 5 ml of N,N-diethylformamide. 0.7 ml (7.5 mmol) of phosphorus oxychloride is then added dropwise in the course of 10 minutes while cooling by means of an ice bath. After stirring for a further 30 minutes, the mixture is allowed to warm to room temperature. During this, an exothermic reaction starts. After stirring for 45 minutes at room temperature, the mixture is heated for 15 minutes at 80° C. to complete the reaction. After cooling, the mixture is put onto 50 ml of ice-water for hydrolysis, the pH is adjusted to 5–6 by means of ammonium acetate, and the mixture is left to stand overnight.

The solid which has precipitated is isolated and recrystallized from ethanol.
Yield: 1.33 g (78%) 37 Melting point: 122° C. (ethanol)
IR: 1635 cm$^{-1}$ (CO)
UV/VIS (37) $\lambda_{max}$ [nm] (lg ε):

| (Acetonitrile) | 342(4.324), 268(3.495) |
| (Chloroform) | 350(4.329), 268(3.513) |

MS (70 eV) m/z (%) (37):
244, 243, 242 (14, 14, 100) [M$^+$], 229, 228, 227 (13, 11, 91)
C$_{10}$H$_{10}$OS$_3$ (242.37)

Calculated: C 49.56 H 4.16 S 39.68
Found: C 49.59 H 4.15 S 39.72

25. 2-(4-(5-Methylthio-thieno[3,2-b]thiophen-2-ylmethyleneamino)phenyl)-ethanol (38)

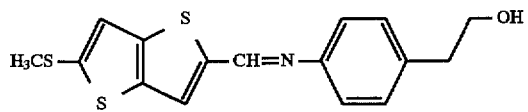

1.0 g (4.7 mmol) of the aldehyde 16, 0.8 g (5.8 mmol) of 2-(4-aminophenyl)ethanol and 600 mg of anhydrous magnesium sulfate are heated under reflux for 4 hours in 6 ml of dry methanol. After cooling to room temperature, the crude product which has precipitated is isolated, washed with water and recrystallized from chloroform.

Yield: 1.39 g (89%) 38 Melting point: 152° C. (chloroform)
IR: 3262 cm$^{-1}$ (OH), 3078, 2919, 2855 (CH)
MS (70 eV) m/z (%) (38):
335, 334, 333 (10, 14, 64) [M$^+$], 304, 303, 302 (15, 19, 100) [M$^+$—CH$_3$]
C$_{16}$H$_{15}$NOS$_3$ (333.48)
Calculated: C 57.63 H 4.53 N 4.20 S 28.84
Found: C 57.72 H 4.57 N 4.04 S 28.84

μβ Estimates of various thieno[3,2-b]thiophenes

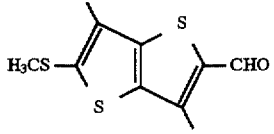  9

Molecular weight: [231.3]
Concentration: [3.0×10$^{-3}$] g/L
Absorption area: [1577.4] cm$^{-1}$
Chromophore length: [1.5] (MNA=1)
RESULTS:
Resonance wavelengths in CHCl$_3$ (nm): 405.3
Resonance wavelengths in CH$_3$CN (nm): 407.7
Solvent shift (cm$^{-1}$): 148
Band intensity (10$^{-17}$): 1.9
μ*β (830 nm) (10$^{-45}$): 1.886 esu. Debye
μ*β (1064 nm) (10$^{-45}$): 0.185 esu. Debye
μ*β (1800 nm) (10$^{-45}$): 0.088 esu. Debye
μ*β (∞ nm)(10$^{-45}$): 0.066 esu. Debye 19

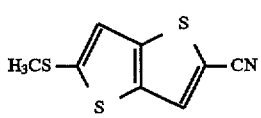  10

Molecular weight: [211.30]
Concentration: [0.0109] g/L
Absorption area: [4380.0] cm$^{-1}$
Chromophore length: [1.7] (MNA=1)
RESULTS:
Resonance wavelength in CHCl$_3$ (nm): 322.0
Resonance wavelength in CH$_3$CN (nm): 324.0
Solvent shift (cm$^{-1}$): 192
Band intensity (10$^{-17}$): 1.0
μ*β (830 nm) (10$^{-45}$): 0.130 esu. Debye
μ*β (1064 nm) (10$^{-45}$): 0.076 esu. Debye
μ*β (1800 nm) (10$^{-45}$): 0.052 esu. Debye μ*β (∞ nm) (10⁻⁴⁵): 0.044 esu. Debye

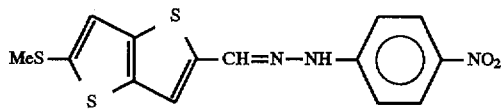

Molecular weight: [349.44]
Concentration: [0.0110] g/L
Absorption area: [5384.0] cm⁻¹
Chromophore length: [2.7] (MNA=1)
RESULTS:
Resonance wavelength in CHCl₃ (nm): 424.0
Resonance wavelength in CH₃CN (nm): 426.0
Solvent shift (cm⁻¹): 111
Band intensity (10⁻¹⁷): 2.8
μ*β (830 nm) (10⁻⁴⁵): −14.447 esu. Debye
μ*β (1064 nm) (10⁻⁴⁵): 1.525 esu. Debye
μ*β (1800 nm) (10⁻⁴⁵): 0.637 esu. Debye
μ*β (∞ nm) (10⁻⁴⁵): 0.468 esu. Debye

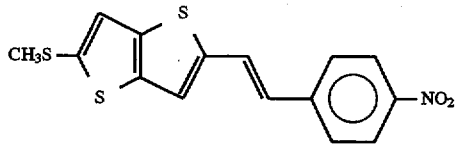

Molecular weight: [333.44]
Concentration: [0.0100] g/L
Absorption area: [4356.0] cm⁻¹
Chromophore length: [2.7] (MNA=1)
RESULTS:
Resonance wavelength in CHCl₃ (nm): 414.0
Resonance wavelength in CH₃CN (nm): 404.0
Solvent shift (cm⁻¹): 597
Band intensity (10⁻¹⁷): 2.3
μ*β (830 nm) (10⁻⁴⁵): −546.462 esu. Debye
μ*β (1064 nm) (10⁻⁴⁵): −5.945 esu. Debye
μ*β (1800 nm) (10⁻⁴⁵): −2.665 esu. Debye
μ*β (∞ nm) (10⁻⁴⁵): −1.990 esu. Debye

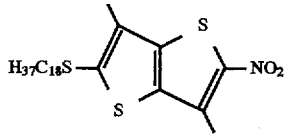

Molecular weight: [497.81
Concentration: [0.0109] g/L
Absorption area: [2180.0] cm⁻¹
Chromophore length: [1.7] (MNA=1)
RESULTS:
Resonance wavelength in CHCl₃ (nm): 392.0
Resonance wavelength in CH₃CN (nm): 386.0
Solvent shift (cm⁻¹): −397
Band intensity (10⁻¹⁷): 1.5
μ*β (830 nm) (10⁻⁴⁵): −2.296 esu. Debye
μ*β (1064 nm) (10⁻⁴⁵): −0.487 esu. Debye
μ*β (1800 nm) (10⁻⁴⁵): −0.249 esu. Debye
μ*β (∞ nm) (10⁻⁴⁵): −0.192 esu. Debye

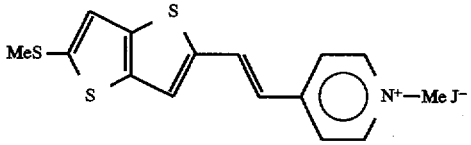

Molecular weight: [431.37]
Concentration: [0.0125] g/L
Absorption area: [3487.0] cm⁻¹
Chromophore length: [2.7] (MNA=1)
RESULTS:
Resonance wavelength in CHCl₃ (nm): 458.0
Resonance wavelength in CH₃CN (nm): 430.0
Solvent shift (cm⁻¹): −1422
Band intensity (10⁻¹⁷): 2.1
μ*β (830 nm) (10⁻⁴⁵): 35.071 esu. Debye
μ*β (1064 nm) (10⁻⁴⁵): −25.212 esu. Debye
μ*β (1800 nm) (10⁻⁴⁵): −7.672 esu. Debye μ*β (∞ nm) (10⁻⁴⁵): −5.317 esu. Debye

EXAMPLE 15

The compound (20) described in Example 13 was spread by the Langmul-Blodgett method on a water surface and compressed. A glass slide was cleaned and rinsed with high-purity water; after this, the slide surface was hydrophilic. The slide was immersed through the monolayer at the air/water interface. Due to the hydrophilic character of the substrate, no layer was transferred. The slide was then removed with a shear of 25 mN/m at a speed of 10 mm/minute through the interface. In this way, a highly ordered monolayer was transferred to the slide.

The slide was mounted in a measuring instrument for frequency-doubling by the maker-fringes method, and the intensity of the harmonic wave generated in the monolayer was measured at a wavelength of 1064 nm. From this, values of 19 pM/V for $X^{(2)}_{zzz}$ and of 5.4 pm/V for $X^{(2)}_{zxx}$ for the monolayer were determined.

EXAMPLE 16

The compound (16) described in Example 6 was commuted in a mortar. The unsieved powder was mounted, using a spacer of about 0.2 mm, between two glass slides. A reference sample of 2-methyl-4-nitroaniline (MNA) was prepared in the same way. The samples were irradiated with light from a pulsed Nd: YAG laser (wavelength 1064 nm, pulse length 5 ns) and the intensity of the forward-scattered harmonic light at 532 nm was measured. The harmonic intensity of the thienothiophene compound was about one tenth of the intensity of MNA.

EXAMPLE 17

The compound (16) described in Example 6 was dissolved at a concentration of 7 mg/l in chloroform, acetonitrile, 2-propanol and hexane, and the absorption spectra were measured. The resonance energies were
28,250 cm⁻¹ in chloroform
28,570 cm⁻¹ in acetonitrile
28,570 cm⁻¹ in 2-propanol
28,940 cm⁻¹ in hexane.

The integrated absorption cross-section for the transition was 1.4×10⁻¹⁷ cm². From these values, a value of 0.574× 10⁻⁴⁵ esu can be estimated for the product of the hyperpolarizability β and the dipole moment μ at an application wavelength of 830 nm.

EXAMPLE 18

The compound (17) described in Example 7 was dissolved at a concentration of 6 mg/l in chloroform, acetonitrile, 2-propanol and hexane, and the absorption spectra were measured. The resonance energies were 22,830 cm⁻¹ in chloroform 22,360 cm$^{-1}$ in acetonitrile
23,470 cm$^{-1}$ in 2-propanol
24,510 cm$^{-1}$ in hexane.

The integrated absorption cross-section for the transition was 2.7×10$^{-17}$ cm$^2$. From these values, a value of 11×10$^{-45}$ esu can be estimated for the product of the hyperpolarizability β and the dipole moment μ at an application wavelength of 830 nm.

EXAMPLE 19

The compound (18) described in Example 8 was dissolved at a concentration of 3.4 mg/l in 2-propanol and hexane, and the absorption spectra were measured. The resonance energies were
30,670 cm$^{-1}$ in 2-propanol
30,490 cm$^{-1}$ in hexane.

The integrated absorption cross-section for the transition was 2.4×10$^{-17}$ cm$^2$. From these values, a value of 0.8×10$^{-45}$ esu can be estimated for the product of the hyperpolarizability β and the dipole moment μ.

We claim:

1. A compound of the formula (I)

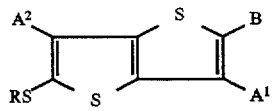

in which

R is a $C_1$- to $C_{22}$-alkyl radical, $A^1$ and $A^2$ are hydrogen or methyl or $A^1$ is hydrogen and $A^2$ is the nitro group and B is an electron-attracting group with a double bond which is in conjugation with the thieno[3,2-b]thiophene ring system.

2. A compound as claimed in claim 1, wherein R is a $C_{12}$- to $C_{22}$-alkyl radical.

3. A layer element containing at least one ordered monomolecular layer of an amphiphilic compound on a support, wherein the amphiphilic compound is a compound as claimed in claim 1.

4. A method of layering the compound of claim 1 in an optical wave guide comprising positioning said compound as a layer in the optical wave guide.

5. A method of layering the compound of claim 1 in an optical frequency multiplier comprising positioning said compound as a layer in the optical frequency multiplier.

* * * * *